United States Patent [19]

Fischer et al.

[11] 4,025,544
[45] May 24, 1977

[54] O-ALKYLSULFONYLGLYCOLIC ANILIDES

[75] Inventors: Adolf Fischer, Mutterstadt; Hanspeter Hansen, Ludwigshafen; Wolfgang Rohr, Mannheim, all of Germany

[73] Assignee: BASF Aktiengesellschaft, Ludwigshafen (Rhine), Germany

[22] Filed: Jan. 22, 1976

[21] Appl. No.: 651,230

Related U.S. Application Data

[63] Continuation of Ser. No. 506,294, Sept. 16, 1974, abandoned.

[30] Foreign Application Priority Data

Oct. 1, 1973 Germany .......................... 2349256

[52] U.S. Cl. ............................. 260/456 A; 71/103
[51] Int. Cl.$^2$ .................................... C07C 143/68
[58] Field of Search ................. 260/456 A; 71/103

[56] References Cited

UNITED STATES PATENTS

| 3,536,721 | 10/1970 | Soong et al. | 260/456 A |
| 3,849,467 | 11/1974 | Mangold et al. | 260/456 A |

*Primary Examiner*—James O. Thomas, Jr.
*Assistant Examiner*—Nicky Chan
*Attorney, Agent, or Firm*—Keil, Thompson & Shurtleff

[57] ABSTRACT

New and valuable 0-(alkylsulfonyl)-glycolic anilides having a good herbicidal action, herbicides containing these compounds, a process for controlling the growth of unwanted plants with these compounds, and a process for their production.

15 Claims, No Drawings

O-ALKYLSULFONYLGLYCOLIC ANILIDES

This application is a continuation of application, Ser. No. 506,294, which was filed on Sept. 16, 1974, now abandoned.

The present application relates to new and valuable O-(alkylsulfonyl)-glycolic anilides, their production and use as herbicides, and herbicides containing these compounds.

It is known (German Pat. No. 1,014,380) to use chloroacetic acid-N-isopropylanilide as herbicide. However, its herbicidal action is poor.

We have now found that O-(alkylsulfonyl)-glycolic anilides of the formula

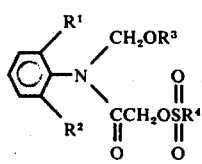

where $R^1$ and $R^2$ denote alkyl of 1 to 4 carbon atoms, $R^3$ denotes alkyl of 1 to 6 carbon atoms, alkoxyalkyl, haloalkyl, alkenyl, haloalkenyl, alkynyl, cycloalkyl or heterocycloalkyl, and $R^4$ denotes alkyl, haloalkyl, cycloalkyl, alkenyl, haloalkenyl or aralkyl, have a good herbicidal action.

$R^1$ and $R^2$ may for instance be methyl, ethyl, propyl, isopropyl, butyl, isobutyl, sec-butyl and tert-butyl.

$R^3$ may for example be methyl, ethyl, propyl, isopropyl, butyl, isobutyl, tert-butyl, n-amyl, branched amyl, n-hexyl, branched hexyl, 2-chloroethyl, 2,2,2-trifluoroethyl, 1,3-dichloroisopropyl, 1,3-dibromoisopropyl, methoxyethyl, methoxyethoxyethyl, allyl, propargyl, butyn-1-yl-3,3-methylbutyn-1-yl-3 and cyclopropyl.

$R^4$ may for instance be methyl, chloromethyl, ethyl, 2-chloroethyl, propyl, isopropyl, butyl, isobutyl, sec-butyl, tert-butyl, pentyl, cyclopentyl, hexyl, cyclohexyl, benzyl, vinyl, allyl, butenyl and hexenyl.

The new compounds have a very good herbicidal action on grass weeds, including millet species.

The new compounds may be prepared by various processes, e.g.

1) Reaction of substituted N-chloromethyl-O-alkylsulfonylglycolic anilides with an alcohol $R^3OH$ in accordance with the following equation:

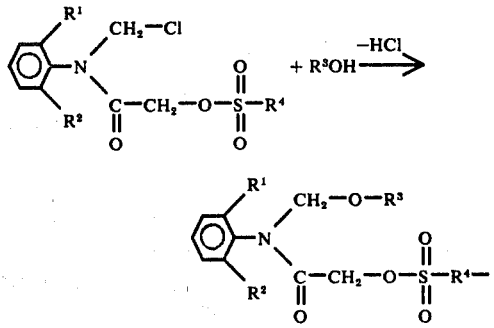

$R^1$, $R^2$, $R^3$ and $R^4$ having the above meanings.

The reaction is carried out in the presence of an acid-binding agent, the alcohol being preferably employed as alkali metal alcoholate.

The N-chloromethyl-O-alkylsulfonylglycolic anilides may be obtained by addition of O-alkylsulfonylglycolic chloride to N-methylene aniline.

2) In accordance with the following equation:

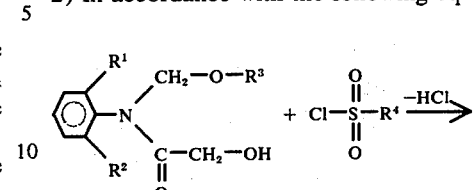

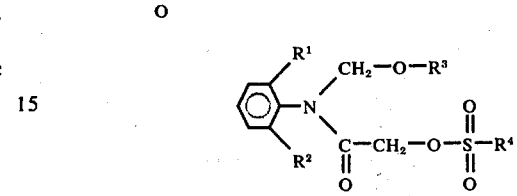

$R^1$, $R^2$, $R^3$ and $R^4$ having the above meanings.

This reaction is also preferably carried out in the presence of an acid-binding agent.

The substituted glycolic anilides may be prepared for instance by the following reactions:

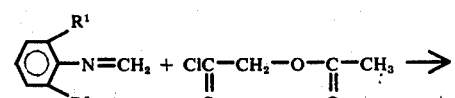

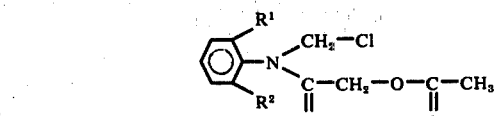

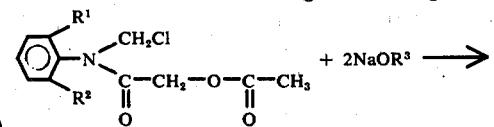

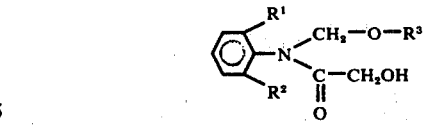

$R^1$, $R^2$ and $R^3$ having the above meanings.

Etherification to the alkoxymethyl group and elimination of the acetyl radical may also be carried out stepwise.

The second manufacturing method is preferred.

EXAMPLE 1

N-chloromethyl-2,6-diethyl-O-methylsulfonylglycolic anilide

At 0° to −3° C and white stirring, a solution of 86.5 parts (by weight) of O-methylsulfonylglycolic chloride and 150 parts of ether was added to a solution of 80.5 parts of N-methylene-2,6-diethyl aniline in 150 parts of ether. After having been stirred for 2 hours at 5° to 10° C the reaction mixture was cooled to 0° C. The precipitated addition product was suction filtered, washed with cold ether and dried in a vacuum desiccator. Melting point: 105° to 107° C.

The compound has the following structural formula:

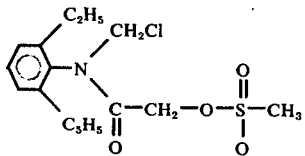

The following compounds may be prepared analogously:

N-chloromethyl-2,6-dimethyl-O-methylsulfonyl-glucolic anilide, m.p. 69° to 70°

N-chloromethyl-2-methyl-6-ethyl-O-methylsulfonyl-glycolic anilide, m.p. 80° to 82° C N-chloromethyl-2,6-diisopropyl-O-methylsulfonyl-glycolic anilide.

O-methylsulfonylglycolic chloride is known from U.S. Pat. No. 3,200,138.

EXAMPLE 2

N-ethoxymethyl-2,6-diethyl-O-methylsulfonylglycolic anilide

A sodium ethylate solution prepared from 9.2 parts of sodium and 250 parts of ethanol was added, at 15° to 25° C, to a solution of 133.4 parts of N-chlormethyl-2,6-diethyl-O-methylsulfonylglycolic anilide in 400 parts of ethanol. The reaction solution was stirred for 1 hour at room temperature, and concentrated in vacuo after removal of the precipitated sodium chloride. The residue was dissolved in 300 parts of ethyl acetate and extracted twice with water. The organic solution was dried with magnesium sulfate, and, upon concentration in vacuo, left a sirupy residue which crystallized out slowly at room temperature; m.p. 38° to 41° C.

The analytically pure substance (m.p. 43° to 44° C) was obtained by crystallization from an ether/ligroin mixture.

The compound has the following structural formula:

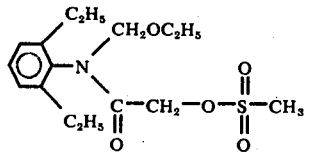

The following compounds may be prepared analogously:

N-methoxymethyl-2,6-diethyl-O-methylsulfonyl-glycolic anilide, m.p. 57° to 58° C N-propoxymethyl-2,6-diethyl-O-methylsulfonyl-glycolic anilide, $n_D^{25} = 1.5115$ N-isopropoxymethyl-2,6-diethyl-O-methylsulfonyl-glycolic anilide, $n_D^{25} = 1.5130$ N-butoxymethyl-2,6-diethyl-O-methylsulfonylglycolic anilide, $n_D^{25} = 1.5080$ N-isobutoxymethyl-2,6-diethyl-O-methylsulfonyl-glycolic anilide, $n_D^{25} = 1.5085$ N-sec-butoxymethyl-2,6-diethyl-O-methylsulfonyl-glycolic anilide N-tert-butoxymethyl-2,6-diethyl-O-methylsulfonyl glycolic anilide N-methoxyethoxymethyl-2,6-diethyl-O-methylsulfonylglycolic anilide N-allyloxymethyl-2,6-diethyl-O-methylsulfonylglycolic anilide N-methoxymethyl-2,6-dimethyl-O-methylsulfonyl-glycolic anilide, m.p. 64° to 65° C N-ethoxymethyl-2,6-dimethyl-O-methylsulfonyl-glycolic anilide, m.p. 60° to 62° C N-propoxymethyl-2,6-dimethyl-O-methylsulfonyl-glycolic anilide, $n_D^{25} = 1.5155$ N-isopropoxymethyl-2,6-dimethyl-O-methylsulfonyl-glycolic anilide, $n_D^{25} = 1.5130$ N-butoxymethyl-2,6-dimethyl-O-methylsulfonyl-glycolic anilide N-isobutoxymethyl-2,6-dimethyl-O-methylsulfonyl-glycolic anilide N-allyloxymethyl-2,6-dimethyl-O-methylsulfonyl-glycolic anilide N-methoxymethyl-2-methyl-6-ethyl-O-methylsulfonyl-glycolic anilide, m.p. 44° to 45° C N-ethoxymethyl-2-methyl-6-ethyl-O-methylsulfonyl-glycolic anilide N-propoxymethyl-2-methyl-6-ethyl-O-methylsulfonyl-glycolic anilide N-isopropoxymethyl-2-methyl-6-ethyl-O-methylsulfonylglycolic anilide N-butoxymethyl-2-methyl-6-ethyl-O-methylsulfonyl-glycolic anilide N-isobutoxymethyl-2-methyl-6-ethyl-O-methylsulfonylglycolic anilide N-sec-butoxymethyl-2-methyl-6-ethyl-O-methylsulfonylglycolic anilide N-methoxyethoxymethyl-2-methyl-6-ethyl-O-methylsulfonylglycolic anilide N-methoxymethyl-2,6-diisopropyl-O-methylsulfonyl-glycolic anilide N-ethoxymethyl-2,6-diisopropyl-O-methylsulfonyl-glycolic anilide N-propoxymethyl-2,6-diisopropyl-O-methylsulfonyl-glycolic anilide N-isopropoxymethyl-2,6-diisopropyl-O-methylsulfonylglycolic anilide N-butoxymethyl-2,6-diisopropyl-O-methylsulfonyl-glycolic anilide N-isobutoxymethyl-2,6-diisopropyl-O-methylsulfonyl-glycolic anilide N-methoxymethyl-2-methyl-6-isopropyl-O-methylsulfonylglycolic anilide N-ethoxymethyl-2-methyl-6-isopropyl-O-methylsulfonylglycolic anilide N-propoxymethyl-2-methyl-6-isopropyl-O-methylsulfonylglycolic anilide N-isopropoxymethyl-2-methyl-6-isopropyl-O-methylsulfonylglycolic anilide

EXAMPLE 3

N-chloromethyl-2,6-diethyl-O-acetylglycolic anilide

At 0° C and while stirring, a solution of 161 parts of N-methylene-2,6-diethyl aniline in 250 parts of ether was added to a solution of 136.5 parts of acetoxyacetyl chloride in 150 parts of dry ether. To complete the reaction the mixture was stirred for 2 hours at 25° C. The small amount of undissolved material was removed and the clear solution concentrated in vacuo. 250 parts of ligroin was added and the whole cooled with ice water, after which the crystalline product was suction filtered; m.p. 51° to 54° C.

The analytically pure product melted at 56° to 58° C after dissolution in, and reprecipitation from, an ether/ligroin mixture.

The compound has the following structural formula:

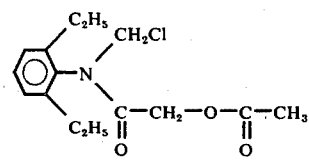

The following compounds were prepared analogously:
N-chloromethyl-2,6-dimethyl-O-acetylglycolic anilide
N-chloromethyl-2,6-methyl-6-ethyl-O-acetylglycolic anilide
N-chloromethyl-2,6-diisopropyl-O-acetylglycolic anilide
N-chloromethyl-2-methyl-6-isopropyl-O-acetylglycolic anilide

EXAMPLE 4

N-methoxymethylglycolic acid-2,6-diethyl anilide

At 15° to 20° C and while stirring, 131 parts of a 33wt% solution, additionally diluted with 100 parts of methanol, of sodium methylate in methanol was added to a solution of 119 parts of N-chloromethyl-2,6-diethyl-O-acetylglycolic anilide in 400 parts of methanol.

To complete the reaction the solution was stirred for 15 hours at room temperature. The mixture was then neutralized and concentrated in vacuo. The residue was dissolved with ethyl acetate and washed twice with water. The organic solution was dried with magnesium sulfate and concentrated in vacuo. The sirupy residue was purified by distillation.

Boiling point (0.05 mm): 120° to 125° C $n_D^{25}$: 1.5255
The compound has the following structural formula:

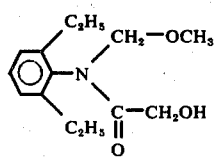

The following compounds were prepared analogously:
N-ethoxymethylglycolic acid-2,6-diethyl anilide b.p. (0.01 mm) 136° to 141° C, $n_D^{25}$ = 1.5176
N-propoxyethylglycolic acid-2,6-diethyl anilide
N-isopropxymethylglycolic acid-2,6-diethyl anilide b.p. (0.01 mm) 125° to 134° C, $n_D^{25}$ = 1.5146
N-butoxymethylglycolic acid-2,6-diethyl anilide b.p. (0.01 mm) 147° to 154° C, $n_D^{25}$ = 1.5112
N-isobutoxymethylglycolic acid-2,6-diethyl anilide
N-methoxymethylglycolic acid-2,6-dimethyl anilide
N-ethoxymethylglycolic acid-2,6-dimethyl anilide
N-propoxymethylglycolic acid-2,6-dimethyl anilide
N-isopropoxymethylglycolic acid-2,6-dimethyl anilide
N-butoxymethylglycolic acid-2,6-dimethyl anilide
N-sec-butoxymethylglycolic acid-2,6-dimethyl anilide
N-isobutoxymethylglycolic acid-256-dimethyl anilide
N-methoxymethylglycolic acid-2-methyl-6-ethyl anilide
N-ethoxymethylglycolic acid-2-methyl-6-ethyl anilide
N-propoxymethylglycolic acid-2-methyl-6-ethyl-anilide
N-isopropoxymethylglycolic acid-2-methyl-6-ethyl anilide
N-butoxymethylglycolic acid-2-methyl-6-ethyl anilide
N-isobutoxymethylglycolic acid-2-methyl-6-ethyl anilide
N-sec-butoxymethylglycolic acid-2-methyl-6-ethyl anilide
N-allyloxymethylglycolic acid-2-methyl-6-ethyl anilide
N-methoxymethylglycolic acid-2,6-diisopropyl anilide
N-ethoxymethylglycolic acid-2,6-diisopropyl anilide
N-propoxymethylglycolic acid-2,6-diisopropyl anilide
N-isopropoxymethylglycolic acid-2,6-diisopropyl anilide
N-butoxymethylglycolic acid-2,6-diisopropyl anilide
N-isobutoxymethylglycolic acid-2,6-diisopropyl anilide
N-sec-butoxymethylglycolic acid-2,6-diisopropyl anilide
N-allyloxymethylglycolic acid-2,6-diisopropyl anilide

EXAMPLE 5

N-ethoxymethyl-2,6-diethyl-O-methylsulfonylglycolic anilide

At 0° to 5° C, a solution of 13.8 parts of methanesulfonyl chloride in 20 parts of dichloromethane was added to a solution of 26.5 parts of N-ethoxyethylglycolic acid-2,6-diethyl anilide and 13.2 parts of triethylamine in 100 parts of dichloromethane. The mixture was stirred for 2 hours at room temperature, and then washed with ice-cold water and sodium bicarbonate solution. The organic solution was dried with magnesium sulfate and concentrated in vacuo. The sirupy residue ($n_D^{25}$: 1.5170) was dissolved in an ether/ligroin mixture and crystallized by cooling with solid $CO_2$/acetone.

Melting point: 43° to 45° C
The compound has the following structural formula:

The following compound were obtained analogously:
N-ethoxymethyl-2,6-diethyl-O-ethylsulfonylglycolic anilide
N-ethoxymethyl-2,6-diethyl-O-propylsulfonylglycolic anilide
N-ethoxymethyl-2,6-diethyl-O-isopropylsulfonylglycolic anilide
N-ethoxymethyl-2,6-diethyl-O-chloromethylsulfonylglycolic anilide
N-ethoxymethyl-2,6-diethyl-O-benzylsulfonylglycolic anilide
N-methoxymethyl-2,6-diethyl-O-ethylsulfonylglycolic anilide
N-methoxymethyl-2,6-diethyl-O-propylsulfonylglycolic anilide
N-methoxymethyl-2,6-diethyl-O-isopropylsulfonylglycolic anilide
N-methoxymethyl-2,6-diethyl-O-chloromethylsulfonylglycolic anilide
N-methoxymethyl-2,6-diethyl-O-benzylsulfonylglycolic anilide N-propoxymethyl-2,6-diethyl-O-ethylsulfonylglycolic anilide
N-propoxymethyl-2,6-diethyl-O-propylsulfonylglycolic anilide
N-propoxymethyl-2,6-diethyl-O-isopropylsulfonylglycolic anilide
N-propoxymethyl-2,6-diethyl-O-chloromethylsulfonylglycolic anilide
N-isopropoxymethyl-2,6-diethyl-O-ethylsulfonylglycolic anilide
N-isopropoxymethyl-2,6-diethyl-O-propylsulfonylglycolic anilide
N-isopropoxymethyl-2,6-diethyl-O-isopropylsulfonylglycolic anilide
N-isopropoxymethyl-2,6-diethyl-O-chloromethylsulfonylglycolic anilide
N-butoxymethyl-2,6-O-ethylsulfonylglycolic anilide
N-butoxymethyl-2,6-diethyl-O-propylsulfonylglycolic anilide
N-butoxymethyl-2,6-diethyl-O-isopropylsulfonylglycolic anilide
N-butoxymethyl-2,6-diethyl-O-chloromethylsulfonylglycolic anilide
N-isobutoxymethyl-2,6-diethyl-O-ethylsulfonylglycolic anilide
N-isobutoxymethyl-2,6-diethyl-O-propylsulfonylglycolic anilide
N-isobutoxymethyl-2,6-diethyl-O-isopropylsulfonylglycolic anilide
N-isobutoxymethyl-2,6-diethyl-O-chloromethylsulfonylglycolic anilide
N-methoxymethyl-2,6-dimethyl-O-ethylsulfonylglycolic anilide
N-methoxymethyl-2,6-dimethyl-O-propylsulfonylglycolic anilide
N-methoxymethyl-2,6-dimethyl-O-isopropylsulfonylglycolic anilide
N-methoxymethyl-2,6-dimethyl-O-chloromethylsulfonylglycolic anilide
N-ethoxymethyl-2,6-dimethyl-O-ethylsulfonylglycolic anilide
N-ethoxymethyl-2,6-dimethyl-O-propylsulfonylglycolic anilide
N-ethoxymethyl-2,6-dimethyl-O-isopropylsulfonylglycolic anilide
N-ethoxymethyl-2,6-dimethyl-O-chloromethylsulfonylglycolic anilide
N-propoxymethyl-2,6-dimethyl-O-ethylsulfonylglycolic anilide
N-propoxymethyl-2,6-dimethyl-O-propylsulfonylglycolic anilide
N-propoxymethyl-2,6-dimethyl-O-isopropylsulfonylglycolic anilide
N-propoxymethyl-O-chloromethylsulfonylglycolic anilide
N-isopropoxymethyl-2,6-dimethyl-O-ethylsulfonylglycolic anilide
N-isopropoxymethyl-2,6-dimethyl-O-propylsulfonylglycolic anilide
N-isopropoxymethyl-2,6-dimethyl-O-isopropylsulfonyl glycolic anilide
N-isopropoxymethyl-2,6-dimethyl-O-chloromethylsulfonylglycolic anilide
N-butoxymethyl-2,6-dimethyl-O-ethylsulfonylglycolic anilide
N-butoxymethyl-2,6-dimethyl-O-propylsulfonylglycolic anilide
N-butoxymethyl-2,6-dimethyl-O-isopropylsulfonylglycolic anilide
N-butoxymethyl-2,6-dimethyl-O-chloromethylsulfonylglycolic anilide
N-isobutoxymethyl-2,6-dimethyl-O-ethylsulfonylglycolic anilide
N-isobutoxymethyl-2,6-dimethyl-O-propylsulfonylglycolic anilide
N-isobutoxymethyl-2,6-dimethyl-O-isopropylsulfonylglycolic anilide
N-isobutoxymethyl-2,6-dimethyl-O-chloromethylsulfonylglycolic anilide Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oil of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts or sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octoylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90% by weight of active ingredient.

There may be added to the compositions or individual active ingredients (if desired, immediately before use (tank-mix)) oils of various types, herbicides, fungicides, nematocides, insecticides, bactericides, trace elements, fertilizers, antifoams (e.g., silicones), growth regulators, antidotes and other herbicidally effective compounds such as
substituted anilines
substituted aryloxycarboxylic acids and salts, esters and amides thereof,
substituted ethers
substituted arsonic acids and their salts, esters and amides
substituted benzimidazoles
substituted benzisothiazoles
substituted benzothiadiazinone dioxides
substituted benzoxazines
substituted benzoxazinones
substituted benzothiadiazoles
substituted biurets
substituted quinolines
substituted carbamates
substituted aliphatic carboxylic acids and their salts, esters and amides
substituted aromatic carboxylic acids and their salts, esters and amides
substituted carbamoylalkylthiol- or -dithiophosphates
substituted quinazolines
substituted cycloalkylamidocarbothiolic acids and their salts, esters and amides
substituted cycloalkylcarbonamidothiazoles
substituted dicarboxylic acids and their salts, esters and amides
substituted dihydrobenzofuranyl sulfonates
substituted disulfides
substituted dipyridylium salts
substituted dithiocarbamates
substituted dithiophosphoric acids and their salts, esters and amides
substituted ureas
substituted hexahydro-1H-carbothioates
substituted hydantoins
substituted hydrazines
substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones
substituted oxadiazolidine diones
substituted oxadiazine diones
substituted phenols and their salts and esters
substituted phosphonic acids and their salts, esters and amides
substituted phosphonium chlorides
substituted phosphonalkyl glycines
substituted phosphites
substituted phosphoric acids and their salts, ester and amides
substituted piperidines
substituted pyrazoles
substituted pyrazole alkylcarboxylic acids and their salts, esters and amides
substituted pyrazolium salts
substituted pyrazolium alkyl sulfates
substituted pyridazines
substituted pyridazones
substituted pyridine carboxylic acids and their salts, esters and amides
substituted pyridines
substituted pyridine carboxylates
substituted pyridones
substituted pyrimidines
substituted pyrimidones
substituted pyrrolidine carboxylic acid and its salts, esters and amides
substituted pyrrolidines
substituted pyrrolidones
substituted arylsulfonic acids and their salts, esters and amides
substituted styrenes
substituted tetrahydrooxadiazine diones
substituted tetrahydroxadiazole diones
substituted tetrahydromethanoindenes
substituted tetrahydroxadiazole thiones
substituted tetranydrothiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the active ingredients or compositions thereof according to the invention.

These agents may be added to the herbicides according to the invention in a ratio by weight of from 1:10 to 10:1. The same applies to oils, fungicides, nematocides, insecticides, bactericides, antidotes and growth regulators.

The amount used of the agents according to the invention may vary and depends in essence on the type of effect to be achieved; it is generally from 0.1 to 15 (and more), preferably from 0.2 to 6, kg per hectare of active ingredient. The agents according to the invention may be used once or several times before or after planting, before sowing, and before, during or after emergence of the crop plants and unwanted plants.

EXAMPLE 6

In the greenhouse, loamy sandy soil was filled into pots and sown with various seeds. The soil prepared in this manner was then immediately treated with 3 kg per hectare of each of the following active ingredients, each being dispersed or emulsified in 500 liters of water per hectare:

I: N-ethoxymethyl-2,6-diethyl-O-methylsulfonylglycolic anilide
III: N-methoxymethyl-2,6-diethyl-O-methylsulfonylglycolic anilide
IV: N-methoxymethyl-2,6-diethyl-O-chloromethylsulfonylglycolic anilide
V: N-methoxymethyl-2,6-diethyl-O-isopropylsulfonylglycolic anilide
VI: N-propoxymethyl-2,6-diethyl-O-methylsulfonylglycolic anilide
VII: N-isopropoxymethyl-2,6-diethyl-O-methylsulfonylglycolic anilide
VIII: N-methoxymethyl-2,6-dimethyl-O-methylsulfonylglycolic anilide
IX: N-ethoxymethyl-2,6-dimethyl-O-methylsulfonylglycolic anilide
X: N-propoxymethyl-2,6-dimethyl-O-methylsulfonylglycolic anilide
XI: N-isopropoxymethyl-2,6-dimethyl-O-methylsulfonylglycolic anilide
XII: N-methoxymethyl-2-methyl-6-ethyl-O-methylsulfonylglycolic anilide
XIV: N-ethoxymethyl-O-methylsulfonylglycolic acid-2-methyl-6-ethyl anilide
XV: N-methoxymethyl-O-ethylsulfonylglycolic acid-2,6-diethyl anilide
XVI: N-propoxymethyl-O-methylsulfonylglycolic acid-2-methyl-6-ethyl anilide
XVII: N-isopropoxymethyl-O-methylsulfonylglycolic acid-2-methyl-6-ethyl anilide
XVIII: N-isobutoxymethyl-O-methylsulfonylglycolic acid-2-methyl-6-ethyl anilide
II: N-isopropyl-α-chloroacetanilide (comparative agent)
XIII: N-methoxymethyl-2-chloroaceto-2,6-diethyl anilide (comparative agent)

After 3 to 4 weeks it was ascertained that active ingredients I, III to XII and XIV to XVIII had a better herbicidal action than comparative compounds II and XIII, combined with the same crop plant compatibility. The results are given below:

| Active ingredient kg/ha | I 3 | II 3 | III 3 | IV 3 | V 3 | VI 3 |
|---|---|---|---|---|---|---|
| Crop plants: | | | | | | |
| Brassica napus | 0 | 0 | 0 | 0 | 0 | 0 |
| Zea mays | 0 | 0 | 0 | 0 | 0 | 0 |
| Sorghum bicolor | 0 | 0 | 0 | 0 | 0 | 0 |
| Glycine max | 0 | 0 | 0 | 0 | 5 | 0 |
| Gossypium hirsutum | 0 | 0 | 0 | 0 | 0 | 0 |
| Beta vulgaris | — | — | 10 | 10 | 0 | 0 |
| Unwanted plants: | | | | | | |
| Lolium multiflorum | 100 | 90 | 95 | 92 | 95 | 90 |
| Poa annua | 100 | 80 | 90 | 90 | 100 | 85 |
| Echinochloa crus-galli | 100 | 75 | 90 | 90 | 90 | 80 |
| Digitaria sanguinalis | 100 | 70 | 80 | 85 | 90 | 75 |
| Setaria faberii | 100 | 80 | 90 | 90 | 95 | 90 |
| Poa trivialis | 100 | 75 | 85 | 80 | 90 | 80 |

| Active ingredient kg/ha | VII 3 | VIII 3 | IX 3 | X 3 | XI 3 | XII 3 | XIII 3 |
|---|---|---|---|---|---|---|---|
| Crop plants: | | | | | | | |
| Brassica napus | 0 | 0 | 0 | 0 | 0 | 0 | 40 |
| Zea mays | 0 | 0 | 0 | 0 | 0 | 0 | 5 |
| Sorghum bicolor | 0 | 0 | 0 | 0 | 0 | 0 | 20 |
| Glycine max | 0 | 0 | 0 | 0 | 0 | 0 | 7 |
| Gossypium hirsutum | 0 | 0 | 0 | 0 | 0 | 0 | 10 |
| Beta vulgaris | 0 | 0 | 0 | 0 | — | 0 | 60 |
| Unwanted plants: | | | | | | | |
| Lolium multiflorum | 90 | 90 | 95 | 95 | 100 | 90 | 90 |
| Poa annua | 82 | 100 | 95 | 100 | 100 | 95 | 90 |
| Echinochloa crus-galli | 80 | 100 | 100 | 100 | 100 | 100 | 95 |
| Digitaria sanguinalis | 76 | 80 | 90 | 90 | 90 | 85 | 95 |
| Setaria faberii | 85 | 90 | 100 | 100 | 100 | 100 | 95 |
| Poa trivialis | 80 | 90 | 90 | 90 | 92 | 90 | 95 |

| Active ingredient kg/ha | XIV 3 | XV 3 | XVI 3 | XVII 3 | XVIII 3 |
|---|---|---|---|---|---|
| Crop plants: | | | | | |
| Brassica napus | 0 | 0 | 0 | 0 | 0 |
| Zea mays | 0 | 0 | 0 | 0 | 0 |
| Sorghum bicolor | 0 | 0 | 0 | 0 | 0 |
| Glycine max | 0 | 0 | 0 | 0 | 0 |
| Gossypium hirsutum | 0 | 0 | 0 | 0 | 0 |
| Unwanted plants: | | | | | |
| Lolium multiflorum | 90 | 95 | 95 | 100 | 100 |
| Poa annua | 90 | 95 | 100 | 95 | 100 |
| Echinochloa crus-galli | 100 | 100 | 100 | 100 | 100 |
| Digitaria sanguinalis | 100 | 100 | 95 | 95 | 100 |
| Setaria faberii | 95 | 100 | 95 | 95 | 100 |
| Poa trivialis | 95 | 95 | 95 | 95 | 100 |

0 = no damage
100 = complete destruction

EXAMPLE 7

In the greenhouse, various plants were treated at a growth height of from 2 to 18 cm with 3 kg per hectare of each of the following active ingredients, each being emulsified or dispersed in 500 liters of water per hectare:

I: N-ethoxymethyl-2,6-diethyl-O-methylsulfonylglycolic anilide
III: N-methoxymethyl-2,6-diethyl-O-methylsulfonylglycolic anilide
IV: N-methoxymethyl-2,6-diethyl-O-chloromethylsulfonylglycolic anilide
V: N-methoxymethyl-2,6-diethyl-O-isopropylsulfonylglycolic anilide
VI: N-propoxymethyl-2,6-diethyl-O-methylsulfonylglycolic anilide
VII: N-isopropoxymethyl-2,6-diethyl-O-methylsulfonylglycolic anilide
VIII: N-methoxymethyl-2,6-dimethyl-O-methylsulfonylglycolic anilide
IX: N-ethoxymethyl-2,6-dimethyl-O-methylsulfonylglycolic anilide
X: N-propoxymethyl-2,6-dimethyl-O-methylsulfonylglycolic anilide
XI: N-isopropoxymethyl-2,6-dimethyl-O-methylsulfonylglycolic anilide
XII: N-methoxymethyl-2-methyl-6-ethyl-O-methylsulfonylglycolic anilide
XIV: N-ethoxymethyl-O-methylsulfonylglycolic acid-2-methyl-6-ethyl anilide
XV: N-methoxymethyl-O-ethylsulfonylglycolic acid-2,6-diethyl anilide
XVI: N-propoxymethyl-O-methylsulfonylglycolic acid-2-methyl-6-ethyl anilide
XVII: N-isopropoxymethyl-O-methylsulfonylglycolic acid-2-methyl-6-ethyl anilide
XVIII: N-isobutoxymethyl-O-methylsulfonylglycolic acid-2-methyl-6-ethyl anilide
II: N-isopropyl-α-chloroacetanilide (comparative agent)
XIII: N-methoxymethyl-2-chloroaceto-2,6-diethyl anilide (comparative agent)

After 3 to 4 weeks it was ascertained that active ingredients I, III to XII and XIV to XVIII had a better herbicidal action than comparative compounds II and XIII, combined with superior compatibility with Glycine max. and Gossypium hirsutum.

The results are given below:

| Active ingredient kg/ha | I 3 | II 3 | III 3 | IV 3 | V 3 | VI 3 | VII 3 |
|---|---|---|---|---|---|---|---|
| Crop plants: | | | | | | | |
| Brassica napus | 0 | 0 | 0 | 0 | 0 | 0 | 0 |
| Zea mays | 0 | 0 | 0 | 0 | 0 | 0 | 0 |
| Sorghum bicolor | 0 | 0 | 0 | 0 | 0 | 0 | 0 |
| Glycine max | 0 | 20 | 0 | 0 | 0 | 0 | 0 |
| Gossypium hirsutum | 0 | 20 | 0 | 0 | 0 | 0 | 0 |
| Beta vulgaris | — | — | — | 0 | 0 | 5 | — |
| Unwanted plants: | | | | | | | |
| Lolium multiflorum | 100 | 40 | 80 | 70 | 70 | 80 | 70 |
| Poa annua | 100 | 25 | 95 | 60 | 64 | 80 | 70 |
| Echinochloa crus-galli | 60 | 30 | 60 | 65 | 60 | 65 | 70 |
| Digitaria sanguinalis | 65 | 50 | 60 | 65 | 60 | 60 | 65 |
| Setaria faberii | 60 | 30 | 65 | 68 | 64 | 65 | 65 |
| Poa trivialis | 100 | 60 | 90 | 80 | 70 | 75 | 75 |

| Active ingredient kg/ha | VIII 3 | IX 3 | X 3 | XI 3 | XII 3 | XIII 3 |
|---|---|---|---|---|---|---|
| Crop plants: | | | | | | |
| Brassica napus | 10 | — | 0 | — | 0 | 30 |
| Zea mays | 0 | 0 | 0 | 0 | 0 | 5 |
| Sorghum bicolor | 0 | 0 | 0 | 0 | 0 | 15 |
| Glycine max. | 0 | 0 | 0 | 0 | 0 | 5 |
| Gossypium hirsutum | 0 | 0 | 0 | 0 | 0 | 5 |
| Beta vulgaris | 0 | 5 | 0 | 5 | 0 | 20 |
| Unwanted plants: | | | | | | |
| Lolium multiflorum | 80 | 70 | 75 | 80 | 70 | 45 |
| Poa annua | 90 | 65 | 70 | 90 | 65 | 50 |
| Echinochloa crus-galli | 70 | 60 | 70 | 75 | 65 | 40 |
| Digitaria sanguinalis | 65 | 60 | 65 | 70 | 60 | 40 |
| Setaria faberii | 70 | 60 | 70 | 75 | 67 | 45 |
| Poa trivialis | 80 | 70 | 70 | 75 | 70 | 40 |

| Active ingredient kg/ha | XIV 3 | XV 3 | XVI 3 | XVII 3 | XVIII 3 |
|---|---|---|---|---|---|
| Crop plants: | | | | | |
| Brassica napus | 0 | 0 | 0 | 0 | 0 |
| Zea mays | 0 | 0 | 0 | 0 | 0 |
| Sorghum bicolor | 0 | 0 | 0 | 0 | 0 |
| Glycine max | 0 | 0 | 0 | 0 | 0 |
| Beta vulgaris | 0 | 0 | 0 | 0 | 0 |
| Unwanted plants: | | | | | |
| Lolium multiflorum | 85 | 70 | 80 | 70 | 90 |
| Poa annua | 90 | 75 | 80 | 70 | 90 |
| Echinochloa crus-galli | 80 | 70 | 75 | 75 | 85 |
| Digitaris sanguinalis | 75 | 75 | 85 | 75 | 85 |
| Setaria faberii | 75 | 75 | 80 | 70 | 85 |
| Poa trivialis | 85 | 80 | 75 | 80 | 90 |

0 = no damage
100 = complete destruction

EXAMPLE 8

90 parts by weight of compound I is mixed with 10 parts by weight of N-methyl-α-pyrrolidone. A mixture is obtained which is suitable for application in the form of very fine drops.

EXAMPLE 9

20 parts by weight of compound I is dissolved in a mixture consisting of 80 parts by weight of xylene, 10 parts by weight of the adduct of 8 to 10 moles of ethylene oxide to 1 mole of oleic acid N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 10

20 parts by weight of compound I is dissolved in a mixture consisting of 40 parts by weight of cyclohexanone, 30 parts by weight of isobutanol, 20 parts by weight of the adduct of 7 moles of ethylene oxide to 1 mole if isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 11

20 parts by weight of compound I is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 party by weight of water and uniformly distributing it therein, an aqueous dispersion is obtained containing 0.02% by weight of the active ingredient.

EXAMPLE 12

20 parts by weight of compound I is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 13

3 parts by weight of compound I is intimately mixed with 97 parts by weight of particulate kaolin. A dust is obtained containing 3% by weight of the active ingredient.

EXAMPLE 14

30 parts by weight of compound I is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:

1. An O-(alkylsulfonyl)-glycolic anilide of the formula

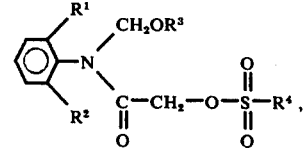

where $R^1$ and $R^2$ denote alkyl of 1 to 4 carbon atoms, $R^3$ denotes alkyl of 1 to 6 carbon atoms or allyl and $R^4$ denotes methyl, chloromethyl, ethyl, 2-chlorethyl, propyl, isopropyl, butyl, isobutyl, sec-butyl, tert-butyl, pentyl, cyclopentyl, hexyl, cyclohexyl, benzyl, vinyl, allyl, butenyl or hexenyl.

2. An anilide as set forth in claim 1 wherein $R^1$ and $R^2$ are ethyl and $R^3$ and $R^4$ are methyl.

3. An anilide as set forth in claim 1 wherein $R^1$ and $R^2$ are ethyl, $R^3$ is ethyl and $R^4$ is methyl.

4. An anilide as set forth in claim 1 wherein $R^1$ and $R^2$ are ethyl, $R^3$ is propyl and $R^4$ is methyl.

5. An anilide as set forth in claim 1 wherein $R^1$ and $R^2$ are ethyl, $R^3$ is isopropyl and $R^4$ is methyl.

6. An anilide as set forth in claim 1 wherein $R^1$ and $R^2$ are ethyl, $R^3$ is methyl and $R^4$ is ethyl.

7. An anilide as set forth in claim 1 wherein $R^1$ and $R^2$ are methyl, $R^3$ is methyl and $R^4$ is methyl.

8. An anilide as set forth in claim 1 wherein $R^1$ and $R^2$ are methyl, $R^3$ is ethyl and $R^4$ is methyl.

9. An anilide as set forth in claim 1 wherein $R^1$ and $R^2$ is methyl, $R^3$ is propyl and $R^4$ is methyl.

10. A anilide as set forth in claim 1 wherein $R^1$ and $R^2$ are methyl, $R^3$ is isopropyl and $R^4$ is methyl.

11. An anilide as set forth in claim 1 wherein $R^1$ is methyl, $R^2$ is ethyl, $R^3$ is methyl and $R^4$ is methyl.

12. An anilide as set forth in claim 1 wherein $R^1$ is methyl, $R^2$ and $R^3$ are ethyl, and $R^4$ is methyl.

13. An anilide as set forth in claim 1 wherein $R^1$ is methyl, $R^2$ is ethyl, $R^3$ is propyl and $R^4$ is methyl.

14. An anilide as set forth in claim 1 wherein $R^1$ is methyl, $R^2$ is ethyl, $R^3$ is isopropyl, and $R^4$ is methyl.

15. An anilide as set forth in claim 1 wherein $R^1$ is methyl, $R^2$ is ethyl, $R^3$ is isobutyl and $R^4$ is methyl.

* * * * *